(12) United States Patent
Erdei et al.

(10) Patent No.: US 6,844,174 B2
(45) Date of Patent: Jan. 18, 2005

(54) FERMENTATION PROCESS FOR LIPSTATIN AND METHOD OF EXTRACTING LIPSTATIN FROM A FERMENTATION BROTH

(75) Inventors: Janos Erdei, Debrecen (HU); Eva Gulyas, Debrecen (HU); Gabor Balogh, Debrecen (HU); Laszlo Toth, Balmazujvaros (HU); Vilmos Keri, Debrecen (HU); Andrea Csorvasi, Debrecen (HU)

(73) Assignee: Biogal Gyogyszergyar Rt., Debrecen (HU)

( * ) Notice: Subject to any disclaimer, the term of this patent is extended or adjusted under 35 U.S.C. 154(b) by 0 days.

(21) Appl. No.: 10/313,603

(22) Filed: Dec. 4, 2002

(65) Prior Publication Data

US 2003/0138919 A1 Jul. 24, 2003

Related U.S. Application Data

(60) Provisional application No. 60/337,218, filed on Dec. 4, 2001, and provisional application No. 60/394,566, filed on Jul. 9, 2002.

(51) Int. Cl.[7] ........................... C12P 17/06; C12P 17/02
(52) U.S. Cl. ........................................ 435/125; 435/123
(58) Field of Search ................................ 435/125, 123

(56) References Cited

U.S. PATENT DOCUMENTS 4,598,089 A    7/1986  Hadvary et al.

FOREIGN PATENT DOCUMENTS

EP    0 129 748 A1 B1    1/1985
EP    0 803 567 A2    10/1997
EP    0 803 576 A2    10/1997

OTHER PUBLICATIONS

B. Borgstrom "Mode of action of tetrahydrolipstatin: a derivative of the naturally occurring lipase inhibitor lipstatin" Biochimica et Biophysica Acta, vol. 962, p. 308–316, (1988).
E.K. Weibel, et al. "Lipstatin, an inhibitor of pancreative lipase, produced by Streptomyces Toxytricini. Part I" the Journal of Antibiotics, vol. XL, No. 8, p. 1081–1085, (1987).
E. Hochuli, et al. "Lipstatin, an inhibitor of pancreative lipase, produced by Streptomyces Toxytricini. Part II" The Journal of Antibiotics, vol. XL, No. 8, p. 1086–1091, (1987).
W. Eisenreich, et al. "Tracer studies with crude U–$^{13}$C–Lipid Mixtures" Journal of Biological Chemistry, vol. 272, No. 2, p. 867–874, (1997).

Primary Examiner—Herbert J. Lilling
(74) Attorney, Agent, or Firm—Kenyon & Kenyon

(57) ABSTRACT

The present invention provides a fermentation process for producing lipstatin comprising the steps of: a) preparing a fermentation medium containing a lipstatin-producing microorganism comprising an oil and an assimilable carbon source, wherein the wt/wt ratio of oil and assimilable carbon source is regulated to achieve an optimal lipstatin biosynthesis by the microorganism; and b) feeding the fermentation medium with an emulsifier, wherein the emulsifier provides an optimal viscosity for the fermentation medium and optimal pH during the fermentation to permit fermentation for lipstatin production. The disclosed process also provides a process for extracting a lipstatin from a fermentation broth.

26 Claims, No Drawings

FERMENTATION PROCESS FOR LIPSTATIN AND METHOD OF EXTRACTING LIPSTATIN FROM A FERMENTATION BROTH

CROSS-REFERENCE TO RELATED APPLICATION

This application claims the benefit under 35 U.S.C. §1.119(e) of Provisional Applications Ser. No. 60/337,218 filed Dec. 4, 2001 and 60/394,566 filed Jul. 9, 2002, the disclosure of which is incorporated by reference in its entirety herein.

FIELD OF THE INVENTION

The present invention relates to a fermentation process for producing lipstatin and a method of extracting lipstatin from a fermentation broth.

BACKGROUND OF THE INVENTION

Obesity and hyperlipidemia are often associated with insulin resistance, diabetes mellitus, hypertension, and cardiovascular diseases, resulting in a high morbidity rate and early mortality. Little is known about the etiology of obesity and hyperlipidemia. The current strategy involves weight control. Several alternate new therapeutic approaches include the use of $\beta_3$-adrenoceptor agonists, CCK-A/cholecystokinin-A-receptor agonists, neuropeptide Y-receptor antagonists and pancreatic lipase inhibitors. The pancreatic lipase inhibitors (orlistat/lipstatin) are among the best candidates.

Lipstatin is a precursor for Orlistat. Upon hydrogenation, lipstatin is converted to form Orlistat. Orlistat has the chemical name (2S, 3S, 5S)-5-[(S)-2-formamido-4-methylvaleryloxy]-2-hexy-3-hydroxyhexadecanoic acid lactone [a/k/a "N-formyl-L-leucine ester with (3S, 4S)-3-hexyl-4-[(2S)-2-hydroxytridecyl]-2-oxetanone", (-)-tetrahydrolipstatin, tetrahydrolipstatin, and orlipastat]. Orlistat has the following chemical formula:

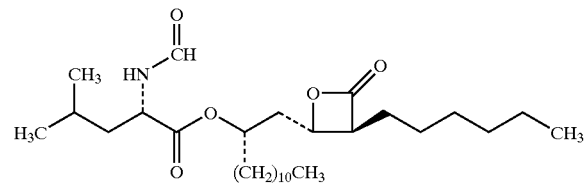

Orlistat

U.S. Pat. No. 4,598,089 is directed to orlistat and its use in treating obesity. Orlistat is currently available for the treatment of obesity. It inhibits lipase enzymes that are responsible for breaking down ingested fat [Borgstrom, B. (1988). Biochem. Biophy. Acta. 962 (3): 308–316], resulting in lipids being digested in the feces rather than being absorbed. Orlistat's inhibition has valuable therapeutic uses, such as control or prevention of hyperlipaemia, atherosclerosis and arteriosclerosis.

Although lipstatin can be synthesized chemically, fermentation to produce lipstatin is more economical. Weibel et al. disclose generally the fermentation process for lipstatin (*Journal of Antibiotics* Vol XL, No.8 pp 1086–1091) and E. Hochuli, et al disclose the structural chemistry for lipstatin (*Journal of Antibiotics* Vol XL, No.8 pp 1081–1085).

U.S. Pat. No. 4,598,089 and Eur. Pat. Appl. 129,748 disclose the cultivation and fermentation of *Streptomyces toxytricini*. The '089 patent discloses the use of a specific Stretomycetes strain (i.e., *Streptomycin toxytricini* [NRRL 15443]) in producing lipstatin.

According to the examples of the U.S. Pat. No. 4,598,089, the vegetative mycelium of *Streptomyces toxytricini* was used for seeding of the inoculum fermentation. After three days incubation, the inoculum fermentation is seeded into a pre-culture medium, and after three additional days incubation this culture serves for seeding the production medium. In the production medium the main carbon sources were potato starch, glucose, ribose and glycerine, and the main nitrogen sources were peptone, soya bean meal, and ammonium-sulphate. During incubation the temperature was maintained at 28° C., aeration was 1 vvm and the mixing speed was 150 rpm. In some examples, lard oil was used in a small quantity (0.1%) as the lipase inductor and anti-foaming agent.

EP 0 803 567 A2 discloses an improved process wherein selected lipstatin precursors were included in the fermentation. These ingredients were linoleic acid, caprylic acid and N-formyl-L-leucine or preferably L-leucine. The yield of the fermentation was low because of the toxicity of the two fatty acids and the amounts of feed solutions were very small. This fermentation process uses a medium that is substantially free of fats and oils because they result in uncontrolled fatty acid liberation during the fermentation and high oil residue at the end of fermentation.

An additional problem with using fats and oils is the question of the emulsion formation. Emulsion formation is important for the microbial consumption of fats but there is no emulsion formation without emulsifier. Eisenreich discloses the use of lecithin as an emulsifier (*Journal of Biological Chemistry*, Vol 272. No. 2, pp. 867–874, 1997). Lecithin may produce a strong emulsion and result in undesirably high viscosity of the fermentation broth which may hinder mixing and aeration during the fermentation. The use of lecithin in lipstatin fermentation may therefore be disadvantageous. There is a continuing need for a desirable emulsifier for use in fermentation processes for producing lipstatin.

U.S. Pat. No. 4,598,089 and Eur. Pat. Appl. 129,748 also disclose the preparation of lipstatin from a fermentation broth of *Streptomyces toxytricini* in the preparation of orlistat. The purification of lipstatin involves multiple chromatographies. The repeated purification processes are costly and impractical for large scale manufacturing. There is a continuing need to improve the isolation and purification of lipstatin from a fermentation broth.

OBJECT AND SUMMARY OF THE INVENTION

The present invention provides a fermentation process for producing lipstatin, comprising the steps of:
a) preparing a fermentation medium containing a lipstatin-producing microorganism and further comprising an oil and an assimilable carbon source, wherein the wt/wt ratio of oil and assimilable carbon source is adjusted to regulate lipstatin biosynthesis by the microorganism; and
b) introducing an emulsifier to the fermentation broth to regulate the fermentation broth viscosity to regulate the production of lipstatin production.

Preferably, the wt/wt ratio of oil and assimilable carbon source is at least 2:1. More preferably, the wt/wt ratio of oil and assimilable carbon source is at least 3:1 Most preferably, the wt/wt ratio of oil and assimilable carbon source is at least 5:1.

Preferably, the quantity of oil fed into the fermentation broth is not less than 5% (wt/wt) and not more than 15% (wt/wt).

Preferably, the oil is selected from the group consisting of a natural oil, a synthetic oil and a mixture thereof. The natural oil is selected from the group consisting of Soya been oil, palm oil, sunflower oil, flax oil, rape seed oil, and corn germ oil. Preferably, the synthetic oil is a synthetic fatty acid glyceride. Preferably, the synthetic oil is selected from the group consisting of AGRIMUL GTO 39 G/glycerol trioleate and AGRIMUL FAC 18 SB/unsaturated C-18 vegetable fatty acid.

Preferably, the emulsifier is a natural emulsifier. More preferably, the natural emulsifier is lecithin. Preferably, the emulsifier is a synthetic, non-consumable emulsifier. More preferably, the synthetic, non-consumable emulsifier is selected from the group consisting of Triton-X-100, Triton-X-45, Brij.35, Igepal/octoxynol as the Triton-X-100 and a mixture thereof.

Preferably, the amount of synthetic emulsifier fed into the fermentation broth is 0.01% (vol/vol) to 0.6% (vol/vol) of the fermentation broth. More preferably, the amount of synthetic and natural emulsifier of emulsifier is equal to or less than 1.3% (vol/vol).

Preferably, the assimilable carbon source is selected from the group consisting of glucose, fructose, saccharose, maltose, and glycerol.

Preferably, the viscosity of the fermentation broth is controlled at least below 1,000 mPascal secundum. More preferably, the viscosity of the fermentation broth is controlled at 300–400 mPascal secundum. Preferably, the feeding of emulsifier is performed at the beginning of the fermentation process.

Preferably, the present invention provides a fermentation process of lipstatin, comprising the step of regulating pH of the fermentation broth. More preferably, the pH of the fermentation broth is regulated between about 6.0 to about 7.5. Most preferably, the pH of the fermentation broth is regulated between about 6.5 to about 7.5.

Preferably, the pH is regulated by feeding the fermentation broth with at least one of an acid, a base, or an assimilable carbon source. Preferably, the lipstatin-producing microorganism is *Streptomyces toxytricini*.

The present invention provides a process for separating a lipstatin from a fermentation broth, comprising the steps of:
(a) extracting the lipstatin from a fermentation broth with a first extraction solvent;
(b) concentrating the first extraction solvent;
(c) extracting the lipstatin from the first concentrated extraction solvent with a second extraction solvent;
(d) concentrating the second extraction solvent;
(e) adding a third extraction solvent;
(f) washing the lipstatin in the third extraction solvent with a fourth extraction solvent; and
(g) separating the washed lipstatin from the third extraction solvent.

Preferably, after the step (f) and before step (g), the present invention further comprises the steps of:
(n) extracting lipstatin from the fourth extraction solvent into a third extraction solvent;
(o) combining the washed third extraction solvent of step (f) with third extraction solvent of step (n).

The present invention further provides extracting the lipstatin from a fermentation broth wherein the step (g) comprises the additional steps of:
(h) concentrating the third extraction solvent;
(i) adding a fifth extraction solvent;
(j) extracting the lipstatin from the fifth extraction with a fourth extraction solvent;
(k) concentrating the fourth extraction solvent;
(l) diluting the extraction solvent with a lower alkyl alcohol; and
(m) applying the diluted lower alkyl alcohol solvent to an anion-exchanger to obtain lipstatin.

Preferably, after the step (k) and before step (l) of the additional steps, the present invention further comprises the steps of:
(q) extracting lipstatin into the fifth extraction solvent; and
(r) concentrating the extracted fifth extraction solvent.

Preferably, the first extraction solvent is a water immiscible solvent. Preferably, the first extraction solvent is selected from the group consisting of ethyl acetate, i-butyl acetate, butyl acetate and methyl ethyl ketone. Most preferably, the first extraction solvent is i-butyl acetate.

Preferably, the first extraction is done at a pH about 2 to about 10.5. More preferably, pH is about 5 to about 8. Most preferably, the pH is about 6 to about 7. Preferably, the concentrating step of the first extraction solvent is carried out under reduced pressure and at a temperature less than about 80° C.

Preferably, the second extraction solvent is a lower alkyl alcohol. Preferably, the second extraction solvent is selected from the group consisting of methanol, ethanol, 1-propanol, 2-propanol, 1-butanol, i-butanol, tert-butanol, acetonitrile, and acetic acid. More preferably, the second extraction solvent is methanol. Preferably, the concentrating step of the second extraction solvent is carried out under reduced pressure and at a temperature less than about 80° C.

Preferably, the third extraction solvent is acetonitrile.

Preferably, the fourth extraction solvent serves to wash lipstatin present in the third extraction solvent. Preferably, the fourth extraction solvent is a hydrocarbon solvent. More preferably, the fourth extraction solvent is selected from the group consisting of pentane, hexane, cyclohexane and heptane. Most preferably, the fourth extraction solvent is hexane or heptane.

Preferably, the fourth extraction solvent serves to extract lipstatin from the fifth extraction solvent.

Preferably, the fifth extraction solvent is a mixture of lower alkyl alcohol and water. More preferably, the fifth extraction solvent is a mixture of lower alkyl alcohol. More preferably, the fifth extraction solvent is a mixture of methanol and water. More preferably, the volume to volume ratio of methanol to water is about 70:15.

Preferably, the steps (l) and (m) are performed using a lower alkyl alcohol. More preferably, the lower alkyl alcohol is methanol. Preferably, the extracting step is carried out under reduced pressure and at a temperature of less than about 80° C.

Preferably, the anion-exchanger is an anion-exchanger resin. More preferably, the anion-exchanger resin is Amberlite™ IRA.

DETAILED DESCRIPTION OF THE INVENTION

Definitions:

As used herein, the terms: "vvm" refers to volume/volume/min; "rpm" refers to revolution per min; "ppm" refers to part per million; and "mPa.s" refers to millipascal secundum.

As used herein, the term "fermentation broth" refers to the fermentation culture medium containing a lipstatin producing microorganism. Preferably, the microorganism is a bacterium. Preferably, the lipstatin producing bacteria include Streptomyces (a genus of gram-positive spore forming bacteria that grow slowly in soil or water as a branching filamentous mycelium similar to that of fungi. A preferred lipstatin producing Streptomyces is *Streptomyces toxytricini*, which also include many different *Streptomyces toxytricini* strains (e.g., *Streptomycin toxytricini* NRRL 15443).

As used herein, the term "lipstatin" refers to a precursor of orlistat. Orlistat, also known as tetrahydrolipstatin, has four more hydrogens than lipstatin Thus, the conversion of lipstatin to orlistat requires hydrogenation.

As used herein, the term "oil" is used interchangeable with "fat". Oil is referred to as a carbon source or a precursor of carbon source.

As used herein, the term "emulsifier" refers to a substance which can be used to produce an emulsion from two liquids that normally cannot be mixed together (such as oil and water). An emulsion refers to a preparation of one liquid distributed in small globules, i.e., a discontinuous phase throughout the body of a second liquid, i.e., a continuous phase.

As used herein, the term "Triton X-100" refers to octylphenol ethylene oxide condensate which is a nonionic detergent. It was a registered trademark formerly owned by Rohm and Haas Co., but now owned by Union Carbide. The "X" series of Triton detergents are produced from octylphenol polymerized with ethylene oxide. The number ("–100") relates only indirectly to the number of ethylene oxide units in the structure. X-100 has an "average of 9.5" ethylene oxide units per molecule. A nonionic detergent refers to a detergent in which the hydrophilic head group is uncharged.

As used herein, the term "extraction solvent" may refer to a solvent used to extract lipstatin from the fermentation broth. Of course, all extraction solvent function as solvent and may also be used as washing solvent, e.g., fourth extraction solvent.

Extraction solvent is a hydrophobic solvents may be a hydrophobic or hydrophilic solvent. Exemplary hydrophobic solvents include i-butyl acetate and ethyl acetate and exemplary hydrophilic solvents include alcohols.

As used herein, the term "alcohol" refers to alkyloxides. Examples for alcohol include methanol, ethanol, propanol or butanol.

As used herein, the term "under reduced pressure" refers to less than atmospheric pressure (760 mmHg).

As used herein, the term "ion-exchanger" preferably refers to an anion-exchanger.

As used herein, the term "extraction yield %" refers to the % of the ratio of the amount of lipstatin present in the fermentation broth before and after the extraction step.

As used herein, the term "overall yield" refers to the average yield.

As used herein, the term "linoleic acid" refers to an impurity or precursor that is present in the fermentation broth and after the addition of second extraction solution is an impurity.

As used herein, the term "impurity" refers to compounds that are present in the fermentation broth other than lipstatin before, during or after the purification steps. An example of impurity includes linoleic acid.

Supplying the fermentation broth with precursors (e.g., linoleic acid) is beneficial to the lipstatin biosynthesis. Because of the toxicity of fatty acids it has to be fed very carefully. Many natural oils contain linoleic acid in its glycerol ester form. *Streptomyces toxytricini* also produces lipase, and depending on the pH of broth the lipase can liberate linoleic acid in different quantities.

Preferably, the fermentation broth is fed with fat in sufficiently high amount to permit good fermentation and lipstatin production. Typically, the amount of fat is in excess than that of that amount of assimilable carbon. Preferably, the wt/wt ratio of oil and assimilable carbon source in the fermentation broth is at least 2:1, more preferably, the ratio is 3:1 and most preferably, the ratio is 5:1 or higher.

Preferably, the fat includes natural fat, synthetic fat or a mixture thereof. The natural fat may include, but not limited to, soya bean oil, palm oil, sunflower oil, flax oil, rape seed oil, and corn germ oil. Synthetic oil includes, but are not limited to, AGRIMUL GTO 39G/glycerol trioleate and AGRIMUL FAC 18 SB/C-18 unsaturated vegetable fatty acids and mixtures thereof. Preferably, the amount of fat is not less than 5% (wt/wt) and not more than 15% (wt/wt) of the fermentation broth.

The relationship between the pH of the fermentation broth and the actual concentration of linoleic acid which is liberated from the oil content of the fermentation broth is illustrated in Table 1, below.

TABLE 1

| pH | Concentration of Linoleic Acid |
|---|---|
| 6.0 | 200 ± 50 ppm |
| 6.5 | 600 ± 100 ppm |
| 7.0 | 1,000 ± 200 ppm |
| 7.5 | 1,700 ± 300 ppm |
| 8.0 | 3,500 ± 500 ppm |

With *Streptomyces toxytricini*, the toxic level of linoleic acid in liquid culture is about 2,300–3,000 ppm. We found that if the pH of lipstatin fermentation broth was not higher than about 7.0 to about 7.5, the linoleic acid liberation and linoleic acid consumption were balanced, and the actual concentration of linoleic acid was not more than about 0.15 to about 0.2%, consequently not reaching the toxic level. For this reason, the pH of lipstatin fermentation was controlled so that the linoleic acid being liberated from fats and oils was enough for the lipstatin biosynthesis but not raised to a toxic level.

Preferably, the pH of the fermentation broth is regulated at about 6.0 to about 7.0. Most preferably, the pH of the fermentation broth is regulated at about 6.5 to about 7.0.

Preferably, the pH of the fermentation broth is regulated by feeding the fermentation broth with an acid, a base or an assimilable carbon source. Preferred assimilable carbon sources include, but are not limited to, glucose, fructose, saccharose, maltose, and glycerol.

Preferably, oils or fats are used as an assimilable carbon source. It is beneficial to use an emulsifier for enhancing the oil consumption. In the presence of an emulsifier, the oil forms a macroscopically homogenous emulsion with the aqueous phase. In addition, the emulsifier increases the bioavailability of oil as a lipstatin precursor for the microorganisms. The efficiency of the emulsification could be monitored by the lipstatin intermediates (e.g., linoleic acid) and lipstatin formation.

We found that a properly selected emulsifier was an important factor in regulating the viscosity of the fermentation broth. It is known that the soya lecithin (see in *Journal of Biological Chemistry*, Vol. 272. No. 2. Pp. 867–874, 1997) results in a highly viscous emulsion. We found that if a synthetic emulsifier was used instead of lecithin, a lesser amount was enough for the emulsification and regulating the viscosity of the broth, e.g., about five times less than the lecithin needed. When lecithin emulsifier was used it produced extremely high viscosity and the whole aerobic process was stopped by the third day of fermentation and lipstatin biosynthesis stopped as well. Also the dissolved oxygen concentration went to zero, oxygen consumption stopped, and the broth became like a solid foam. As a result, the lipstatin yield was only the half of the expected value.

Among the many main parameters that can influence the emulsification, mixing rate for the fermentation broth is a key factor. Preferably, the mixing rate is increased during the fermentation process. The exact mixing rate may be adjusted according to the dissolved oxygen level present in the fermentation broth. The dissolved oxygen level was monitored with an amperometric oxygen electrode (Mettler Toledo GmbH, Urdorf, Switzerland). The oxygen electrode was calibrated to the air saturated medium (set to be 80%) and to a zero point which was set electronically. The dissolved oxygen level during the fermentation is expected to decrease relative to the saturated oxygen level due to the metabolic oxygen consumption and uptake by the microorganisms. Hence, the mixing rate is preferably increased during the fermentation process to compensate the decrease in dissolved oxygen level and to maintain the dissolved oxygen level at an optimal level.

A preferred viscosity for the fermentation broth is less than 1,000 mPascal secundum. A more preferred viscosity for the fermentation broth is less than 400–500 mPascal secundum. The most preferred viscosity for the fermentation broth is less than 300–400 mPascal secundum. The viscosity of the fermentation broth was measured with a RHEOLAB MC 1 (Paar Physica, Stuttgart, Germany) rotational, shear stress and creep rheometer equipped with a Z3 DIN standard measuring system.

We tested different conventional synthetic emulsifiers including Triton-X-100, Triton-X-45, Brij-35, and Igepal. We found that they were all suitable for the emulsion formation. Optimal concentrations of these synthetic emulsifiers were determined for achieving a condition whereby the maximum viscosity was low enough but the dissolved oxygen level and aerobic metabolic activity were maintained. Ideally, emulsifier is used at a concentration to provide sufficient emulsification such that the particle size of emulsion is small and a homogeneous emulsion is formed. Preferably, agitation is adjusted by changing the mixing rate. Agitation is used to enhance mixing of fermentation broth and allow emulsifier to achieve maximum emulsification effect. Agitation therefore allows adequate oxygen level while maintaining a homogeneous emulsion.

Preferably, the amount of synthetic emulsifier fed into the fermentation broth is 0.01% (vol/vol) to 0.6% (vol/vol) of the fermentation broth. Preferably, the amount of natural and synthetic emulsifier fed into the fermentation broth is equal to or less than 1.3% (vol/vol) of the fermentation broth. The introduction of the emulsifier can occur at the beginning of the fermentation process or during the course of the fermentation process. Preferably, the feeding of emulsifier occurs at the beginning of the fermentation process.

The following alternative embodiments are based on the extraction processes of lipstatin as set forth in the claims.

According to one alternative embodiment of the present invention, lipstatin present in the fermentation broth is extracted using the first extraction solvent. Preferably, the first extraction solvent is a hydrophobic solvent selected from the group consisting of ethyl acetate, i-butyl acetate, butyl acetate and methyl ethyl ketone. More preferably, the first extraction solvent is i-butyl acetate.

Preferably, the first extraction is carried out at a pH of about 2 to about 11. More preferably, the first extraction is carried out at a pH of about 5 to about 8. Most preferably, the first extraction is carried out at a pH of about 6 to about 7.

According to another alterative embodiment, the present invention provides a process for extracting lipstatin from a fermentation broth wherein the concentrated fermentation broth is diluted with the second extraction solvent. Preferably, the second extraction solvent is selected from the group consisting of methanol, ethanol, 1-propanol, 2-propanol, 1-butanol, i-butanol, tert-butanol, acetonitrile and acetic acid. More preferably, the second extraction solvent is methanol.

Preferably, the step of concentrating the second extraction solvent is carried out under reduced pressure and preferably at a temperature of less than about 80° C.

According to another alternative embodiment, the present invention provides a process for extracting lipstatin from a fermentation broth wherein the concentrated fermentation broth is diluted with the third extraction solvent. Preferably, the third extraction solvent is acetonitrile.

According to another alternative embodiment, the present invention provides a process for extracting lipstatin from a fermentation broth wherein the concentrated lipstatin fermentation broth is washed with the fourth extraction solvent. Preferably, the fourth extraction solvent is a hydrocarbon solvent. More preferably, the fourth extraction solvent is selected from the group consisting of pentane, hexane, cyclohexane and heptane.

According to another alternative embodiment, the present invention provides the fourth extraction solvent can function both as a washing solvent and an extraction solvent. While the fourth extraction solvent serves to wash the lipstatin present in the third extraction solvent, it may also serve to re-extract lipstatin that is present in the fifth extraction solvent.

According to the present invention, the extracted lipstatin at this stage attains a high degree of purity. In an alterative alternative embodiment of the present invention, the extraction process of lipstatin can be optionally repeated to improve the purity.

According to yet another alternative embodiment, the present invention provides a process for extracting lipstatin from a fermentation broth wherein the lipstatin present in the third extraction solvent is diluted with fifth extraction solvent. Preferably, the fifth extraction solvent is a mixture of lower alkyl alcohol and water. The fifth extraction solvent can be used without water. Preferably, the fifth extraction solvent is a mixture of methanol and water. More preferably, the volume to volume ratio (v/v) of methanol to water is 70:15.

According to another alterative embodiment, the present invention provides a process for extracting lipstatin from a fermentation broth wherein the extracted lipstatin from the fifth extraction solvent is further extracted using the fourth extraction solvent.

According to another alternative embodiment, the present invention optionally provides a process for extracting lipstatin from a fermentation broth wherein the extracted lipstatin from the fourth extraction solvent is further extracted in the fifth extraction solvent.

According to another alterative embodiment, the present invention optionally provides a process for extracting lipstatin from a fermentation broth wherein the extracted lipstatin from the fifth extraction solvent is concentrated.

According to another alternative embodiment, the present invention provides a process for extracting lipstatin from a fermentation broth wherein the concentrated lipstatin in the fifth extraction solvent is diluted with methanol and the lipstatin in the diluted methanol solvent extracted by subject the methanol solvent to chromatography. Preferably, the chromatographic column used is an anion-exchanger. More preferably, the anion-exchanger is an anion-exchanger resin. Exemplary resin includes Amberlite™ IRA. It is useful to remove the impurities (e.g., lineolic acid) that are present in the fermentation broth.

Preferably, the dilution steps [i.e., additional steps of (l) and (m) is carried out using a lower alkyl alcohol. More preferably, the lower alkyl alcohol is methanol.

According to another alternative embodiment, the extraction processes involving multiple extraction solvents as disclosed herein can be generally used in other fermentation processes, in additional to the lipstatin fermentation process as disclosed herein. One of ordinary skill in the art would appreciate that some conditions for extraction can be modified without affecting the lipstatin obtained.

The present invention is described in further detail with reference to the following examples. However, the scope of the present invention is by no means restricted by these specific examples.

Fermentation Process for Lipstatin

EXAMPLE 1 a) Preparation of a Seed Culture

A seed medium was prepared containing Soya bean flour 10.0 grams, glycerol 5.0 grams, Soya peptone 5.0 grams, Soya oil 10 mL, Triton X-100 0.5 grams in water (1 litre). The pH of the seed medium was adjusted to 6.5±0.1 with a NaOH solution. An inoculum medium (50 mL) was filled into a 500 mL Erlenmeyer flask and closed with a cotton plug and sterilized. Sterilization was performed at 121±2° C., 100±10 kPa for 25 minutes. The sterilized inoculum medium was inoculated with a spore suspension of *Streptomyces toxytricini* and incubated at 28±2° C. for 20–40 hours under aerobic conditions.

b) Main Fermentation Process

About 2–5 vol % of the above seed culture was used for the inoculation of a 500 ml Erlenmeyer flask, which contained 50±5 ml fermentation medium (F-1). The fermentation medium contained Soya bean flour 30 grams, glycerol 7.0 grams, cotton seed meal 1.0 gram, polypropylene glycol 0.20 gram, Soya oil 80 ml, Triton X-100 1.0 gram as an emulsifier in 1 litre tap water. The pH of the fermentation medium was adjusted before sterilization to 7.0±0.1 with NaOH. Sterilization was at 121±2° C., 100±10 kPa for 25 minutes. Fermentation was carried out at 28±2° C. for 6–7 days under aerobic conditions.

After fermentation for 144–168 hours, the concentration of lipstatin was 1,700–1,800 mg/l.

Isolation of Lipstatin

The lipstatin (active ingredient) was isolated from the fermentation broth using a standard purification method. 50 ml fermentation broth was extracted with the organic solvents (150 ml acetone and 100 ml hexane). After the separation of the organic layer, the aqueous layer was extracted three times with 100 ml of a 1:1 mixture of acetone and hexane. The combined organic extracts were dried with sodium sulfate and concentrated to oil form. The oil was dissolved in hexane (35 ml) and chromatographed using silica gel column. The column was developed with hexane 40 ml and 300 ml hexane ethyl acetate mixture (20:1), 200 ml hexane ethyl acetate mixture (10:1) and finally 200 ml hexane ethyl acetate mixture (5:1). After evaporation of solvent, the yield was 95 mg crude material containing 60 mg lipstatin (63% purity).

The viscosity of the fermentation broth was measured with a RHEOLAB MC 1 (Paar Physica, Stuttgart, Germany) rotational, shear stress and creep rheometer equipped with a Z3 DIN standard measuring system. The thermostated (25° C.) measuring cup was filled with 10 ml of fermentation broth and the rheological curve (by gradually increasing shear rate) and viscosity (at D=10 s-1 speed) were determined. The viscosity of the fermentation broth was obtained in mPascal secundum and was determined to be 300–400 mPascal secundum.

EXAMPLE 2

The seed culture (80 ml) of Example 1 was used to inoculate on a laboratory scale. The stirred fermentor with a vessel size of 7 litres contained 4.0 litres of the main fermentation medium (F-2). Composition of the main fermentation medium included Soya bean flour 120.0 grams, glycerol 28.0 grams, cotton seed meal 4.0 grams, polypropylene glycol 1.0 gram, Soya oil 320 ml, Triton X-100 6.0 grams as an emulsifier in 4 litres. The pH of the fermentation medium was adjusted to 7.0±0.1 with NaOH before sterilization. Incubation was carried out at 28±2° C. for 6–7 days under aerobic condition (1,500 rpm, 1 vvm).

The amount of lipstatin was 1,500–1,600 mg/l after an incubation period of 144–168 hours. The viscosity of the fermentation broth was 400–500 mPascal secundum as determined with the instrument: Anton Paar Rheolab MCI MS Z3 DIN D=10 s-1.

EXAMPLE 3

About 2–5 vol. % of the seed culture of Example 1 was used to inoculate a 500 ml Erlenmeyer flask which contained 50±5 ml of fermentation medium (F-2). The fermentation medium (F-2) contained the following ingredients: Soya bean flour 30 grams, glycerol 7.0 grams, cotton seed meal 1.0 gram, polypropylene glycol 0.20 gram, Soya oil 80 ml, Brij 35 S 3.0 grams as an emulsifier in 1 litre tap water. The pH of the fermentation medium was adjusted to 7.0±0.1 with NaOH. Sterilization was done at 121±2° C., 100±10 kPa, for 25 minutes. Fermentation was carried out at 28±2° C. for 6–7 days under aerobic conditions.

The amount of lipstatin was 1,300–1,400 mg/l after an incubation period of 144–168 hours. The viscosity of the fermentation broth was 600–700 mPascal secundum as determined with the instrument: Anton Paar Rheolab MCI MS Z3 DIN D=10 s-1.

EXAMPLE 4

About 2–5 vol % of the seed culture of Example 1 was used to inoculate a 500 ml Erlenmeyer flask, which contained 50±5 ml of fermentation medium (F-3).The fermentation medium (F-3) contained the following ingredients: Soya bean flour 30 grams, glycerol 7.0 grams, cotton seed meal 1.0 gram, polypropylene glycol 0.20 gram, Soya oil 80 ml, Soya lecithin 12 gram as an emulsifier in 1 litre tap water. The pH of the fermentation medium was adjusted to 7.0±0.1 with NaOH. Sterilization was done at 121±2° C., 100±10 kPa for 25 minutes. Fermentation was carried out at 28±2° C. for 6–7 days under aerobic conditions.

The amount of lipstatin was 1,200–1,300 mg/l after an incubation period of 144–168 hours. The viscosity of the fermentation broth was 1,600–1,700 mPascal secundum as determined with the instrument: Anton Paar Rheolab MCI MS Z3 DIN D=10 s-1.

EXAMPLE 5

80 ml of the seed culture of Example 1 was used to inoculate a lab scale fermentor with a vessel size of 7 litres that contained 4.0 litres of fermentation medium F3. The fermentation medium contained Soya bean flour 120.0 grams, glycerol 28.0 grams, cotton seed meal 4.0 grams, polypropylene glycol 1.0 gram, Soya oil 320 ml, Soya lecithin 48 grams as emulsifier in 4 litres. The pH of the fermentation medium was adjusted to 7.0±0.1 with NaOH before sterilization. Incubation was carried out under aerobic conditions (1,000 rpm, 1 vvm) at 28±2° C. for 6–7 days.

The titre of lipstatin was 600–700 mg/l after an incubation period of 144–168 hours. The viscosity of the fermentation broth was 2,200–2,500 mPascal secundum as determined with the instrument: Anton Paar Rheolab MCI MS Z3 DIN D=10 s-1.

The analysis of the samples was performed by HPLC, using RP C 18 type, 5 micron column. The mobile phase was a mixture of acetonitrile and 0.1% phosphoric acid in a v/v ratio of 8 to 2. Detection was done by UV detector at 205 nm wavelength.

Extraction of Lipstatin from a Fermentation Broth

EXAMPLE 6

A fermentation broth (3.4 kg) containing lipstatin was extracted with i-butyl acetate (step a) at a pH of about 2.0 to about 10.5. The extraction achieved a yield of 94%.

The i-butyl acetate phase was further washed with water at a pH of about 3.0 to about 8.0.

The washed i-butyl acetate phase was concentrated (step b) in a vacuum at a maximum temperature of about 80° C. The concentrated i-butyl acetate phase (311.9 grams) contained the lipstatin (1.305 gram) and was then extracted (step c) three times with methanol. The methanol phases were combined. The combined methanol phases contained 1,100 gram of lipstatin. The overall yield of the steps was about 79%.

EXAMPLE 7

A methanol phase was produced according to Example 6.

The methanol phase (936 ml) was concentrated (step d) under reduced pressure to an oily residue (20.39 grams). The oily residue was diluted (step e) with acetonitrile (125 ml). The diluted solution contained the lipstatin (1,100 gram).

The acetonitrile solution was washed (step f) three times with hexane. The hexane phases were combined (step n) (300 ml) and washed three times with acetonitrile (10 ml). The acetonitrile phases were combined (step o). The combined acetonitrile phases contained the lipstatin (952 mg) product to be separated (step g). The combined solution was concentrated in vacuum at a maximum temperature of about 60° C. The mass of concentrate was 4.95 grams. The yield of this step was about 87%.

EXAMPLE 8

An acetonitrile concentrate was produced according to Example 7.

The concentrate (4.95 grams) was diluted (step i) with a methanol:water (70:15) mixture (85 ml) resulting in a diluted solution containing lipstatin. The diluted solution containing lipstatin (952 mg) was extracted (step j) five times with hexane (85 ml). The hexane phases were combined and concentrated (step k)in vacuum at a maximum temperature of about 60° C. to a volume of 85 ml.

The concentrated hexane solution was extracted (step q) five times with methanol:water (70:15) mixture (85 ml). The combined methanol:water phase was concentrated (step r) in vacuum at a maximum temperature of about 80° C. to an oily residue (1.267 gram). The oily residue contained lipstatin (748 mg). The yield of the step was about 86%.

EXAMPLE 9

An oily residue was produced according to Example 8.

The oily residue (603 mg) was diluted (step l) with methanol (10 ml). The diluted solution contained lipstatin (356 mg) and was passed through an anion-exchanger (step m) [15 ml]. The type of anion-exchanger used was Amberlite™ IRA 67 resin in hydroxide form. The resin was washed with methanol. Fractions containing lipstatin were collected. Volume of the combined fractions was 20 ml. The combined fractions contained about 302 mg lipstatin and about 142 mg other substances.

EXAMPLE 10

A lipstatin containing 302 mg active substance was produced according to Example 9.

The lipstatin was hydrogenated in the presence of a catalyst in a methanol solution. The hydrogenation of about 302 mg lipstatin resulted in about 270 mg orlistat (tetrahydrolipstatin).

EXAMPLE 11

Lipstatin was extracted according to Example 6, but instead of methanol, one of ethanol, 1-propanol:water mixture, 2-propanol:water mixture, 1-butanol:water mixture, i-butanol:water mixture, tert-butanol:water mixture, acetonitrile, acetic acid was used as the extraction solvent.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosure of which are incorporated by reference in their entireties.

What is claimed is:

1. A fermentation process for producing lipstatin, comprising:
    fermenting a fermentation broth comprising a fermentation medium and a lipstatin-producing microorganism, the fermentation medium comprising an oil and a non-oil assimilable carbon source, wherein the wt/wt ratio of the oil and non-oil assimilable carbon source is adjusted to regulate lipstatin biosynthesis by the microorganism, and
    wherein the fermentation broth further comprises an emulsifier having at least a synthetic emulsifier to regulate the fermentation broth viscosity in order to regulate lipstatin production.

2. The process according to claim 1, wherein the wt/wt ratio of the oil and non-oil assimilable carbon source is at least 2:1.

3. The process according to claim 1, wherein the wt/wt ratio of the oil and non-oil assimilable carbon source is at least 3:1.

4. The process according to claim 1, wherein the wt/wt ratio of the oil and non-oil assimilable carbon source is at least 5:1.

5. The process according to claim 1, wherein the quantity of oil in the fermentation broth is not less than 5% (wt/wt) and not more than 15% (wt/wt).

6. The process according to claim 1, wherein the oil is selected from the group consisting of a natural oil, a synthetic oil and a mixture thereof.

7. The process according to claim 6, wherein the natural oil is selected from the group consisting of Soya bean oil, palm oil, sunflower oil, flax oil, rape seed oil, and corn germ oil.

8. The process according to claim 6, wherein the synthetic oil is a synthetic fatty acid glyceride.

9. The process according to claim 6, wherein the synthetic oil is selected from the group consisting of glycerol trioleate and unsaturated C-18 vegetable fatty acid.

10. The process according to claim 1, farther comprising the step of isolating lipstatin from the fermentation broth.

11. The process according to claim 1, wherein the emulsifier further comprises a natural emulsifier.

12. The process according to claim 11, wherein the natural emulsifier is lecithin.

13. The process according to claim 1, wherein the at least a synthetic emulsifier is a synthetic, non-consumable emulsifier.

14. The process according to claim 13, wherein the synthetic, non-consumable emulsifier is selected from the group consisting of Triton-X-100, Triton-X-45, polyoxyethylene lauryl ether, and a mixture thereof.

15. The process according to claim 1, wherein the amount of the at least a synthetic emulsifier in the fermentation broth is 0.01% (vol/vol) to 0.6% (vol/vol) of the fermentation broth.

16. The process according to claim 1, wherein the amount of the emulsifier is equal to or less than 1.3% (vol/vol).

17. The process according to claim 1, wherein the non-oil assimilable carbon source is selected from the group consisting of glucose, fructose, saccharose, maltose, and glycerol.

18. The process according to claim 1, wherein the viscosity of the fermentation broth is controlled at least below 1,000 mPascal secundum.

19. The process according to claim 1, wherein the viscosity of the fermentation broth is controlled at 300–400 mPascal secundum.

20. The process according to claim 1, wherein the emulsifier is added at the beginning of the fermentation process.

21. The process according to claim 1, further comprising the step of regulating pH of the fermentation broth.

22. The process of claim 21, wherein the pH of the fermentation broth is regulated between about 6.0 to about 7.5.

23. The process of claim 21, wherein the pH of the fermentation broth is regulated between about 6.5 to about 7.5.

24. The process of claim 21, wherein the pH is regulated by feeding the fermentation broth with at least one of an acid, a base, or an assimilable carbon source.

25. The process of claim 1, wherein the lipstatin-producing microorganism is *Streptomyces toxytricini*.

26. The process according to claim 13, wherein the synthetic, non-consumable emulsifier is Triton-X-100, and the Triton-X-100 is octoxynol.

* * * * *